United States Patent
Schneider et al.

(10) Patent No.: US 11,925,926 B2
(45) Date of Patent: Mar. 12, 2024

(54) PLATINUM COMPLEXES HAVING FERROCENE DIPHOSPHINE LIGANDS FOR CATALYSIS OF THE HYDROXYCARBONYLATION OF ETHYLENICALLY UNSATURATED COMPOUNDS

(71) Applicant: EVONIK OPERATIONS GMBH, Essen (DE)

(72) Inventors: Carolin Schneider, Monheim am Rhein (DE); Ralf Jackstell, Rostock (DE); Matthias Beller, Ostseebad Nienhagen (DE); Robert Franke, Marl (DE)

(73) Assignee: EVONIK OXENO GMBH & CO. KG, Marl (DE)

( * ) Notice: Subject to any disclaimer, the term of this patent is extended or adjusted under 35 U.S.C. 154(b) by 225 days.

(21) Appl. No.: 17/544,144

(22) Filed: Dec. 7, 2021

(65) Prior Publication Data

US 2022/0176360 A1    Jun. 9, 2022

(30) Foreign Application Priority Data

Dec. 9, 2020 (EP) .................................... 20212752

(51) Int. Cl.
   *C07C 51/06* (2006.01)
   *B01J 31/16* (2006.01)
   *C07C 51/00* (2006.01)

(52) U.S. Cl.
   CPC ........... *B01J 31/1616* (2013.01); *C07C 51/00* (2013.01); *C07C 2531/22* (2013.01)

(58) Field of Classification Search
   CPC ................................ C07C 51/06; B01J 31/16
   See application file for complete search history.

(56) References Cited

U.S. PATENT DOCUMENTS

| | | |
|---|---|---|
| 9,688,604 B2 | 6/2017 | Jennerjahn et al. |
| 9,725,398 B2 | 8/2017 | Dong et al. |
| 10,077,228 B2 | 9/2018 | Dong et al. |
| 10,202,329 B2 | 2/2019 | Dong et al. |
| 10,294,191 B2 | 5/2019 | Dong et al. |
| 2021/0299645 A1 | 9/2021 | Yang et al. |
| 2021/0300957 A1 | 9/2021 | Yang et al. |

FOREIGN PATENT DOCUMENTS

EP      3 121 186 A2    1/2017

OTHER PUBLICATIONS

U.S. Appl. No. 17/544,227, Yang et al., filed Dec. 7, 2021.
U.S. Appl. No. 17/544,179, Schneider et al., filed Dec. 7, 2021.
U.S. Appl. No. 17/544,254, Schneider et al., filed Dec. 7, 2021.
European Search Report dated May 10, 2021 for European Patent Application No. 20212752.8 (6 pages In German with Machine Translation).
Yang, J., et al. A general platinum-catalyzed alkoxycarbonylation of olefins. Chemical Communications. 2020. vol. 56, pp. 5235-5238.
Nabavizadeh, M.S., et al. Assembly of Cyclometalated Platinum(II) Complexes via 1,1'-Bis(diphenylphosphino)ferrocene Ligand: Kinetics and Mechanisms. Organometallics. 2011. vol. 30, pp. 1466-1477.
Miesel, D., et al. Electron-Transfer Studies of trans-Platinum Bis(acetylide) Complexes. European Journal of Inorganic Chemisty. 2014. pp. 5541-5553.
Kiso, Y., et al. Silicon hydiides and nickel complexes. Journal of Organometallic Chemistry. 1973. vol. 50, pp. 297-310.
Gramigna, K. M., et al. Palladium(II) and Platinum(II) Compounds of 1,1'-Bis(phosphino)metallocene (M = Fe, Ru) Ligands with Metal-Metal Interactions. Organometallics. 2013. vol. 32, pp. 5966-5979.
Meier, M., et al. Lumineszente Eisen-Platin-Mehrkemkomplexe mit funktionalisierten Acetyliden. [Luminescent Iron-Platinum Multinuclear Complexes with Functionalized Acetylides]. Zeitschrift Fur Anorganische Und Allgemeine Chemie. 2008. vol. 634, pp. 2235-2240 (In German with English Abstract and Machine Translation).

*Primary Examiner* — Caixia Lu
(74) *Attorney, Agent, or Firm* — Smith, Gambrell & Russell, LLP

(57) ABSTRACT

Platinum complexes having ferrocene-diphosphine ligands for catalysis of the hydroxycarbonylation of ethylenically unsaturated compounds.

9 Claims, No Drawings

PLATINUM COMPLEXES HAVING FERROCENE DIPHOSPHINE LIGANDS FOR CATALYSIS OF THE HYDROXYCARBONYLATION OF ETHYLENICALLY UNSATURATED COMPOUNDS

The present invention relates to platinum complexes having ferrocene-diphosphine ligands for catalysis of the hydroxycarbonylation of ethylenically unsaturated compounds.

The hydroxycarbonylation of ethylenically unsaturated compounds is a process of increasing significance. A hydroxycarbonylation is understood to mean the direct reaction of ethylenically unsaturated compounds such as olefins with carbon monoxide in the presence of a metal or a metal complex and a ligand to give the corresponding acids:

Scheme 1: General reaction equation of the hydroxycarbonylation of an ethylenically unsaturated compound

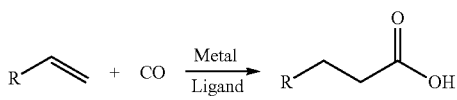

Ferrocene-based compounds and use thereof in alkoxycarbonylation are described in EP 3121186 A2. The catalyst used here is a Pd complex comprising these ligands.

A disadvantage of palladium is its high cost.

The technical problem addressed by the present invention is that of providing novel complexes having a less costly metal than palladium as the central atom. The complexes are additionally to achieve good conversions in hydroxycarbonylations.

This object is achieved by the complex shown below.

Complex comprising Pt and a compound of formula (I)

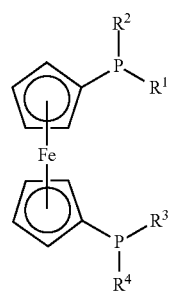

(I)

where
$R^1$, $R^2$, $R^3$, $R^4$ are each independently selected from —$(C_1$-$C_{12})$-alkyl, —$(C_6$-$C_{20})$-heteroaryl.

The expression $(C_1$-$C_{12})$-alkyl encompasses straight-chain and branched alkyl groups having 1 to 12 carbon atoms. These are preferably $(C_1$-$C_8)$-alkyl groups, more preferably $(C_1$-$C_6)$-alkyl groups, most preferably $(C_1$-$C_4)$-alkyl.

The expression $(C_6$-$C_{20})$-heteroaryl encompasses mono- or polycyclic aromatic hydrocarbyl radicals having 6 to 20 carbon atoms, where one or more of the carbon atoms are replaced by heteroatoms. Preferred heteroatoms are N, O and S. The $(C_3$-$C_{20})$-heteroaryl groups have 6 to 20, preferably 6 to 14, particularly preferably 6 to 10 ring atoms. Thus, for example, pyridyl in the context of this invention is a $C_6$-heteroaryl radical.

Suitable $(C_6$-$C_{20})$-heteroaryl groups having at least six ring atoms are especially pyridyl, pyridazinyl, pyrimidyl, pyrazinyl, benzofuranyl, indolyl, isoindolyl.

In one embodiment, at least two of the $R^1$, $R^2$, $R^3$, $R^4$ radicals are a —$(C_6$-$C_{20})$-heteroaryl radical having at least six ring atoms.

In one embodiment, the $R^1$ and $R^3$ radicals are each a —$(C_6$-$C_{20})$-heteroaryl radical having at least six ring atoms.

In one embodiment, the $R^1$ and $R^3$ radicals are each 2-pyridyl.

In one embodiment, $R^2$ and $R^4$ are —$(C_1$-$C_{12})$-alkyl.

In one embodiment, $R^2$ and $R^4$ are tert-butyl.

In one embodiment, the compound (I) has the structure (1):

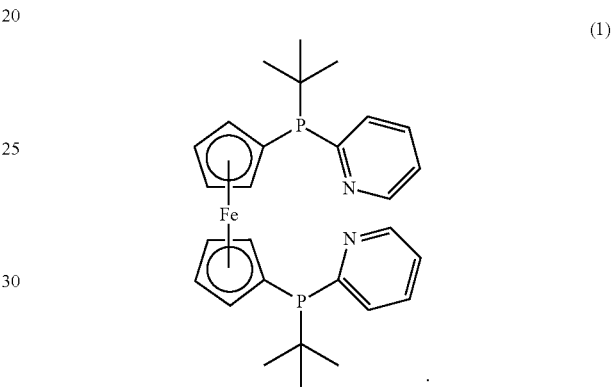

(1)

The invention further relates to the use of a complex according to the invention for catalysis of an hydroxycarbonylation reaction.

Process comprising the process steps of:
a) initially charging an ethylenically unsaturated compound;
b) adding a complex as described above, or a compound of formula (I)

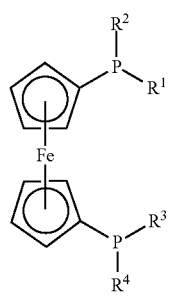

(I)

where
$R^1$, $R^2$, $R^3$, $R^4$ are each independently selected from —$(C_1$-$C_{12})$-alkyl, —$(C_6$-$C_{20})$-heteroaryl and a substance comprising Pt;
c) adding an acid;
d) feeding in CO;
e) heating the reaction mixture from a) to d), with conversion of the ethylenically unsaturated compound to a carboxylic acid.

In this process, process steps a), b), c) and d) can be effected in any desired sequence. Typically, however, the addition of CO is effected after the co-reactants have been initially charged in steps a) to c). In addition, CO can also be fed in in two or more steps, in such a way that, for example, a portion of the CO is first fed in, then the mixture is heated, and then a further portion of CO is fed in.

The ethylenically unsaturated compounds used as reactant in the process according to the invention contain one or more carbon-carbon double bonds. These compounds are also referred to hereinafter as olefins for simplification. The double bonds may be terminal or internal.

In one variant of the process, the ethylenically unsaturated compound does not comprise any further functional groups apart from carbon-carbon double bonds.

In one variant of the process, the ethylenically unsaturated compound is selected from: ethene, propene, 1-butene, cis- and/or trans-2-butene, isobutene, 1,3-butadiene, 1-pentene, cis- and/or trans-2-pentene, 2-methyl-1-butene, 3-methyl-1-butene, 2-methyl-2-butene, hexene, tetramethylethylene, heptene, 1-octene, 2-octene, di-n-butene, or mixtures thereof.

In one variant of the process, the acid in process step c) is selected from: acetic acid, perchloric acid, sulfuric acid, phosphoric acid, methylphosphonic acid, methanesulfonic acid, trifluoromethanesulfonic acid, tert-butanesulfonic acid, p-toluenesulfonic acid (PTSA), 2-hydroxypropane-2-sulfonic acid, 2,4,6-trimethylbenzenesulfonic acid, dodecylsulfonic acid, camphorsulfonic acid.

In one variant of the process, the acid in process step c) is acetic acid (AcOH).

In one variant of the process, the substance comprising Pt is selected from: platinum dichloride ($PtCl_2$), platinum(II) acetylacetonate [$Pt(acac)_2$], platinum(II) acetate [$Pt(OAc)_2$], dichloro(1,5-cyclooctadiene)platinum(II) [$Pt(cod)_2Cl_2$], bis(dibenzylideneacetone)platinum [$Pt(dba)_2$], bis(acetonitrile)dichloroplatinum(II) [$Pt(CH_3CN)_2Cl_2$], (cinnamyl)platinum dichloride [$Pt(cinnamyl)Cl_2$].

In one variant of the process, the substance comprising Pt is selected from: platinum dichloride ($PtCl_2$), platinum(II) acetylacetonate [$Pt(acac)_2$], platinum(II) acetate [$Pt(OAc)_2$].

CO is fed in in step d) preferably at a partial CO pressure between 0.1 and 10 MPa (1 to 100 bar), preferably between 1 and 8 MPa (10 to 80 bar), more preferably between 2 and 6 MPa (20 to 60 bar).

The reaction mixture is heated in step e) of the process according to the invention preferably to a temperature in the range from 60° C. to 160° C., preferably from 80° C. to 140° C., particularly preferably from 80° C. to 120° C., in order to convert the ethylenically unsaturated compound to an acid.

The invention is to be illustrated in detail hereinafter by a working example.

Conversion of 1-octene to the Acid

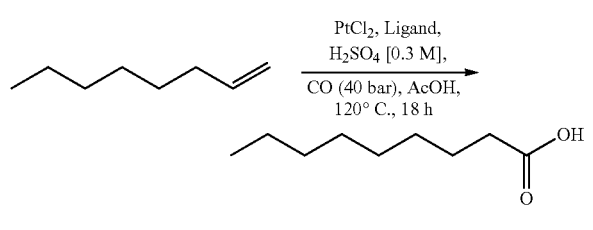

Reaction conditions: 1-octene (1.0 mmol), $PtCl_2$ (0.01 mmol, 1.0 mol %), ligand: bidentate phosphine ligand (0.022 mmol, 2.2 mol %), sulfuric acid [0.3 M] 0.5 mL, AcOH (1.5 mL), pressure (CO): 40 bar, temperature: 120° C., reaction time: 18 h.

The reaction was carried out in a process according to the invention using ligand (1), and also using ligand (2) as a comparative experiment:

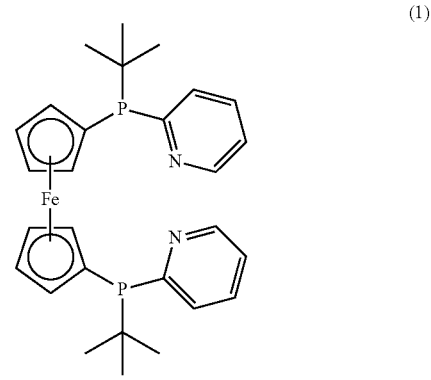

(1)

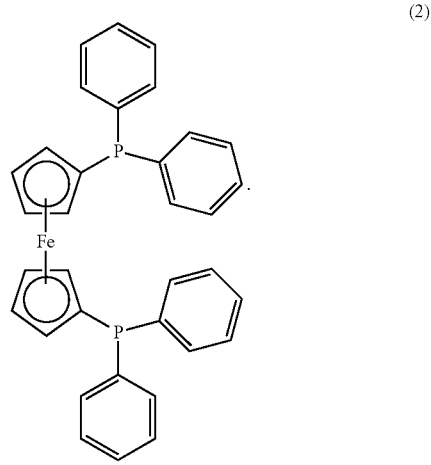

(2)

The process according to the invention using ligand (1) afforded a yield of 41% here. Conversely, in the comparative experiment using ligand (2), a yield of only 13% could be achieved.

The cost of Pt is below that of Pd. The object is thus achieved by a complex according to the invention.

The invention claimed is:

1. A process comprising:
   a) adding an ethylenically unsaturated compound to form a reaction mixture;
   b) adding to the reaction mixture a platinum complex having a ferrocene-diphosphine ligand of formula (I)

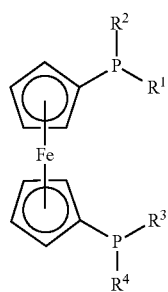

(I)

where
R¹, R², R, and R⁴ are each independently selected from —($C_1$-$C_{12}$)-alkyl, —($C_6$-$C_{20}$)— or heteroaryl or adding to the reaction mixture the ligand of formula (I) and a Pt compound;

c) adding to the reaction mixture an acid;
d) feeding into the reaction mixture CO;
e) heating the reaction mixture formed from a) to d), to convert the ethylenically unsaturated compound to a carboxylic acid.

2. The process according to claim 1,
wherein the ethylenically unsaturated compound is selected from: ethene, propene, 1-butene, cis- and/or trans-2-butene, isobutene, 1,3-butadiene, 1-pentene, cis- and/or trans-2-pentene, 2-methyl-1-butene, 3-methyl-1-butene, 2-methyl-2-butene, hexene, tetramethylethylene, heptene, 1-octene, 2-octene, di-n-butene, or mixtures thereof.

3. The process according to claim 1,
wherein the acid is selected from: acetic acid, perchloric acid, sulfuric acid, phosphoric acid, methylphosphonic acid, methanesulfonic acid, trifluoromethanesulfonic acid, tert-butanesulfonic acid, p-toluenesulfonic acid, 2-hydroxypropane-2-sulfonic acid, 2,4,6-trimethylbenzenesulfonic acid, dodecylsulfonic acid or camphorsulfonic acid.

4. The process according to claim 1,
wherein the acid is acetic acid.

5. The process according to claim 1,
wherein the Pt compound is selected from: platinum dichloride ($PtCl_2$), platinum(II) acetylacetonate [Pt(acac)$_2$], platinum(II) acetate [Pt(OAc)$_2$], dichloro(1,5-cyclooctadiene)platinum(II) [Pt(cod)$_2$Cl$_2$], bis(dibenzylideneacetone)platinum[Pt(dba)$_2$], bis(acetonitrile)dichloroplatinum(II) [Pt(CH$_3$CN)$_2$Cl$_2$] or (cinnamyl)platinum dichloride [Pt(cinnamyl)Cl$_2$].

6. The process according to claim 1,
wherein the Pt compound is selected from: platinum dichloride ($PtCl_2$), platinum(II) acetylacetonate [Pt(acac)$_2$] or platinum(II) acetate [Pt(OAc)$_2$].

7. The process according to claim 1,
wherein the $R^1$ and $R^3$ radicals are each 2-pyridyl.

8. The process according to claim 7,
wherein $R^2$ and $R^3$ are —($C_1$-$C_{12}$)-alkyl.

9. The process according to claim 8,
wherein $R^2$ and $R^4$ are tert-butyl.

* * * * *